United States Patent [19]
Arzoumanidis et al.

[11] 3,932,474
[45] Jan. 13, 1976

[54] PREPARATION OF ANTRAQUINONE
[75] Inventors: Gregory Gerasimos Arzoumanidis, Stamford, Conn.; Francis Clyde Rauch, Warrington, Pa.
[73] Assignee: American Cyanamid Company, Stamford, Conn.
[22] Filed: May 28, 1974
[21] Appl. No.: 473,531

[52] U.S. Cl. ............................ 260/369; 252/441
[51] Int. Cl.² ...................................... C07C 49/68
[58] Field of Search ................. 260/369; 252/441

[56] References Cited
UNITED STATES PATENTS
3,395,183   7/1968   Fenton ............................. 252/441

Primary Examiner—Paul M. Coughlan, Jr.
Attorney, Agent, or Firm—Harry H. Kline

[57] ABSTRACT

There is provided a process for preparing anthraquinone in good yield and purity by subjecting either benzene or benzophenone and carbon monoxide in at least equimolar amounts to the action of either a non-noble metal halide catalyst, such as cupric chloride and ferric chloride, or a noble metal halide catalyst, such as palladium chloride and platinum bromide, or mixtures of said noble and non-noble metal halides at elevated temperatures and pressures.

8 Claims, No Drawings

PREPARATION OF ANTHRAQUINONE

The present invention relates to the preparation of anthraquinone. More specifically, the invention relates to the cyclocarbonylation of benzene or benzophenone utilizing carbon monoxide under elevated pressures and temperatures. Still more specifically, the invention is concerned with the catalytic cyclocarbonylation of benzene or benzophenone in the presence of carbon monoxide under elevated pressures and temperatures utilizing either a noble metal halide or a non-noble metal halide or mixtures thereof to obtain anthraquinone in good yield and purity.

It is known that anthraquinone can be obtained utilizing prior art procedures. One such procedure involves the oxidation of anthracene. Another is directed to the Diels-Alder reaction of butadiene with 1,4-naphthoquinone. Still another process involves the reaction of benzene and phthalic anhydride in the presence of a Friedel-Crafts catalyst, such as aluminum chloride. Although each procedure produces anthraquinone, nonetheless, each is not entirely satisfactory, since the processes are costly and work-up procedures are quite difficult and lengthy in obtaining anthraquinone in good yield and purity. If a process could be devised to overcome the prior practices in terms of cost and ease of work-ups, such a process would fulfill a long sought after need in the art.

It is, therefore, a principal object of the invention to provide a process for synthesizing anthraquinone from an economical source, namely, from either benzene or benzophenone utilizing relatively inexpensive reaction conditions of elevated pressures and temperatures. It is a further object of the invention to catalytically cyclocarbonylate benzene or benzophenone utilizing readily available reaction conditions, starting reactants, and work-up procedures. Other objects and advantages will become apparent from a consideration of the ensuing description.

To these ends, it has been unexpectedly found that anthraquinone can be prepared in an economical manner and in good yield and purity by subjecting benzene or benzophenone and carbon monoxide to the action of a non-noble metal catalyst or a noble metal catalyst or a mixture thereof employing elevated pressures and temperatures. Cyclocarbonylation occurs within two to ten hours with rapid recovery of desired product in good yield.

According to the process of the invention, benzene or benzophenone is reacted with carbon monoxide at elevated temperatures and pressures in the presence of a copper halide, iron halide, cobalt halide, palladium halide or platinum halide catalyst or a mixture of the same to effect cyclocarbonylation of the benzene derivative. In general, at least equimolar amounts of benzene or benzophenone and carbon monoxide are employed in the presence of a non-noble or noble metal catalyst. Exemplary of the latter are cupric chloride, cupric bromide, cupric iodide, ferric chloride, ferric bromide, ferric iodide, cobalt chloride, palladium chloride, palladium bromide, platinum chloride, or a 50/50 mixture of ferric chloride and platinum chloride. Usually, from 1 mol to 1.5 mols of the catalyst per mol of benzene or benzophenone is a good operating practice.

Advantageously, a wide range of temperatures and pressures may be utilized in the present process. For instance, temperatures between about 160°C. and about 300°C. and, preferably, between about 210°C. and about 230°C. are employed under a superatmospheric pressure of from about 200 to about 1000 pounds per inch and, preferably, between 325 and 375 pounds per square inch.

At the completion of the reaction, it is a good practice to rinse the reaction mixture with an inert solvent therefor, with agitation. Exemplary of such solvents are toluene, ethyl ether and dimethyl sulfoxide. The insolubles are separated as by filtration so as to recover the catalyst. The filtrate is next subjected to distillation to remove the solvent and to recover anthraquinone as yellow crystals.

In order to facilitate a further understanding of the invention, the following examples are presented primarily for purposes of illustrating certain more specific details thereof. The invention is not to be deemed limited thereby except as defined in the claims. Unless otherwise noted, all parts are by weight.

EXAMPLE 1

To a suitable high pressure reaction vessel are added 10.2 parts of anhydrous cupric chloride and 12.4 parts of benzophenone. The vessel is tightly closed and then purged with argon followed by the introduction of carbon monoxide to a final pressure of 350 pounds per inch at room temperature. The reaction vessel or autoclave is put into a preheated jacket and maintained at a temperature of from 220°C. to 225°C. for four hours under vigorous rocking of the autoclave. A pressure of about 690 psi is noted.

At the termination of the four hour period, the autoclave is cooled, opened and vented. The contents in the autoclave are next washed down with toluene and the contents collected. A solid residue is obtained upon filtration. The filtrate is next distilled at a temperature of 90°C. under vacuum, whereby the toluene is recovered and the residue remaining analyzes principally as anthraquinone by vapor phase chromatography. This residue is found to amount to a yield of about 90 percent by weight, based on benzophenone.

Similar results are noted where cobalt chloride is substituted for cupric chloride.

EXAMPLE 2

The procedure of Example 1 is repeated in every detail except that benzene is substituted for benzophenone and palladium chloride replaces cupric chloride therein. Similar results are noted in the formation of anthraquinone.

EXAMPLE 3

To a suitable autoclave as in Example 1 above are added 2.9 parts of benzene, 4.7 parts of anhydrous ferric chloride and 5.4 parts of palladium chloride. The reaction is carried out under initial 1000 psig pressure of carbon monoxide at 215°C. — 220°C. for two hours.

There is recovered substantially quantitative yields of anthraquinone, based on the benzene consumed.

Although benzene and benzophenone are exemplified in the above examples, it is clear that the process of the invention is equally applicable to aromatic reactants, such as, for instance, 1-phenylnaphthalene, reacted with carbon monoxide to obtain benzanthrone.

We claim:

1. A process for preparing anthraquinone which comprises the steps of: reacting in the presence of a catalyst selected from the group consisting of a non-noble metal halide, a noble metal halide and mixtures of the same about equimolar amounts of benzene or benzophenone and carbon monoxide for from two to ten hours at a superatmospheric pressure of at least 200 pounds per square inch and at a temperature ranging from about 160°C to about 300°C, and recovering anthraquinone.

2. The process of claim 1 wherein benzene and carbon monoxide are reacted.

3. The process of claim 1, wherein benzophenone and carbon monoxide are reacted.

4. The process of claim 1 wherein the noble metal halide is palladium chloride.

5. The process of claim 1 wherein the non-noble metal halide is cupric chloride.

6. The process of claim 1 wherein the non-noble metal halide is ferric chloride.

7. The process of claim 1 wherein the mixture of non-noble metal halide and noble metal halide comprises a 50/50 mixture of ferric chloride and palladium chloride.

8. The process of claim 1 wherein about equimolar amounts of benzophenone and carbon monoxide are reacted for four hours in the presence of cupric chloride at a temperature ranging from 220°C. and 225°C. and a pressure ranging from about 350 psi to about 690 psi under vigorous agitation, and recovering anthraquinone.

* * * * *